(12) United States Patent
Rex

(10) Patent No.: US 6,298,261 B1
(45) Date of Patent: Oct. 2, 2001

(54) CATHETER TRACKING SYSTEM

(75) Inventor: James Alexander Rex, Romsey (GB)

(73) Assignee: Roke Manor Research Limited, Hants (GB)

( * ) Notice: Subject to any disclaimer, the term of this patent is extended or adjusted under 35 U.S.C. 154(b) by 0 days.

(21) Appl. No.: 09/192,216

(22) Filed: Nov. 16, 1998

(30) Foreign Application Priority Data

Nov. 15, 1997 (GB) .................................................. 9724071

(51) Int. Cl.$^7$ ........................................................ A61B 5/00
(52) U.S. Cl. ............................ 600/424; 600/437; 607/122
(58) Field of Search .................................... 600/424, 407, 600/437, 447, 461; 606/130; 607/122

(56) References Cited

U.S. PATENT DOCUMENTS

| | | |
|---|---|---|
| 4,991,148 | 2/1991 | Gilchrist . |
| 4,995,011 | 2/1991 | Spiesberger . |
| 5,214,617 | 5/1993 | Rouquette . |
| 5,391,199 * | 2/1995 | Ben-Haim .......................... 607/122 |
| 5,515,853 | 5/1996 | Smith et al. . |
| 5,722,402 * | 3/1998 | Swanson et al. ..................... 607/122 |
| 5,782,899 * | 7/1998 | Imran .................................. 607/122 |
| 5,797,849 * | 8/1998 | Vesely et al. ........................ 600/461 |
| 5,899,860 * | 5/1999 | Pfeiffer et al. ...................... 600/424 |
| 5,938,602 * | 8/1999 | Lloyd .................................. 600/424 |
| 5,954,649 * | 9/1999 | Chia et al. ........................... 600/424 |
| 6,019,725 * | 2/2000 | Vesely et al. ........................ 600/447 |
| 6,038,468 * | 3/2000 | Rex ..................................... 600/424 |

FOREIGN PATENT DOCUMENTS 2 314 158 A    12/1997   (GB) .

* cited by examiner

*Primary Examiner*—Teresa Walberg
*Assistant Examiner*—Fadi H. Dahbour
(74) *Attorney, Agent, or Firm*—Crowell & Moring LLP

(57) ABSTRACT

A catheter tracking system for locating and tracking a catheter head 16 with reference to a part of the human or animal body 1 includes a catheter having a catheter head which is arranged to be conveyed through the human or animal body to a desired location and a plurality of spaced apart transducers at least one of which is disposed on the catheter. At least two further transducers are disposed at predetermined reference positions in and/or around the human or animal body. A signal processing unit operates to energize the plurality of transducers, and in accordance with a time of flight of signals between the reference transducers and the transducer disposed on the catheter, to determine the location of the catheter head with respect to the reference transducers. The energized signals consist of predetermined waveforms which when analyzed by the signal processing unit serve to increase an accuracy with which the catheter head location is determined.

14 Claims, 4 Drawing Sheets

CATHETER TRACKING SYSTEM

BACKGROUND OF THE INVENTION

The present invention relates to catheter tracking systems which serve to determine a position of catheters within the human or animal body. Furthermore, the present invention relates to methods for tracking catheters within the human or animal body.

The term catheter as used herein refers to any type of invasive surgical tool, used for insertion into a human or animal body for the purpose of providing remote access to a party of the body for performing some type of investigative and/or medical procedure.

With the increasing use of minimally invasive surgical techniques in medical diagnosis and therapy, there is a need for new methods of remotely locating and tracking catheters or other medical instruments inside a human or animal body. Currently, X-ray fluoroscopic imaging is the standard catheter tracking technique. However, excessive exposure to X-ray dosages by both the patient and clinician can be harmful. Thus, alternative catheter tracking methods are desirable.

Several alternative methods have been published including some which employ magnetic field measurements and others using ultrasonic measurements. One such ultrasonic catheter tracking technique is known as sonomicrometry. Sonomicrometry is based on finding distances between miniature omnidirectional ultrasound transducers by measuring a time taken for ultrasound signals to travel between the ultrasound transducers and then multiplying this by the speed of sound. It is assumed that the average speed of sound in the medium between the transducers is known and that the sound travels along a straight line. Both of these assumptions introduce errors into the distance calculations, ultimately leading to a level of uncertainty in the catheter location.

To locate the tip of a catheter using sonomicrometry, an ultrasound transducer is mounted proximate the catheter tip. A location of this transducer is then determined by measuring a time of flight of acoustic signals from the transducer on the tip to at least four other transducers acting as reference transducers disposed to detect the acoustic signals. The time of flight of the acoustic signals between the transducer on the tip and the reference transducers is representative of a distance of the tip of the catheter to the reference transducers. In combination, these distances serve to provide an indication of a position of the catheter in a three dimensional reference frame defined by the positions of the reference transducers.

A known catheter tracking system based on these sonomicrometric principles is described in U.S. Pat. No. 5,515,853 (Smith et al). This system measures the ultrasound travel times between pairs of transducers using short pulses of sound and clocked digital counters. The counters are started by the electrical pulse which drives the transmitting transducer, and are stopped by the detection of a pulse at the receiving transducer. Detection is accomplished by thresholding the received signal. Each transmitting transducer is activated in turn, after waiting for the last transmitted pulse to arrive at all receiving transducers, and for stray reflections from the various discontinuities inside the body to die away.

A disadvantage of this known catheter tracking system is that ultrasound signals do not travel in a straight line. Additionally, the speed of propagation of any ultrasound wave is dependent upon the material in which it is travelling. Ultrasound waves are subject to absorption, reflection, refraction, and scattering effects due to the material along its path, resulting in a loss of signal strength. An ultrasound wave travelling in the human body will suffer from all of the aforementioned effects, resulting in an error associated with each time of flight measurement, leading to uncertainty in determining the catheter location.

A technical problem of improving an accuracy with which a catheter tip is located is addressed by the catheter tracking system according to the present invention.

SUMMARY OF THE INVENTION

The invention proposed here employs a different method of measuring the time of flight of ultrasound signals, by recording and processing transmitted and received waveforms.

According to the present invention there is provided a catheter tracking system for locating and tracking a catheter head with reference to a part of the human or animal body, said catheter tracking system comprising of a plurality of spaced apart transducers at least one of which is disposed on a catheter and at least two others of which are disposed at predetermined reference points, and a signal processing unit coupled to said plurality of spaced apart transducers and arranged to selectively enable individual ones of said plurality of spaced apart transducers to operate as one of either a transmitter or a receiver, and to energise at least one of said transmitters such that at least one of said transmitters generates at least one transmitted signal which is detected by at least one of said receivers, wherein the time of flight of said at least one transmitted signal generated by said at least one transmitter and received by said at least one receiver is indicative of the distance between said at least one transmitter and said at least one receiver, whereby said times of flight between said at least one transducer disposed on said catheter and said at least two other transducers disposed at said predetermined reference points gives an indication of said location of said catheter with reference to said reference transducers, characterised in that said at least one transmitted signal has a predetermined waveform, and said signal processing unit further operates to compare said at least one transmitted signal generated by said at least one transmitter with a signal representative of said transmitted signal received by said at least one receiver, and consequent upon said comparison determines said time of flight of said at least one transmitted signal to a substantially greater accuracy.

One technique which could be used for comparison of the transmitted signal with the signal representative of the transmitted signal is cross-correlation of pairs of transmitted and received signals.

By cross-correlating the transmitted and received signals an increase in accuracy in the time of flight is effected from a peak produced from the cross-correlation at a temporal displacement corresponding to the time of flight.

The present invention offers several advantages over the prior art for a catheter tracking system. An improvement in the accuracy with which time of flight measurements are determined allows for distance measurements to be made at lower signal-to-noise ratios (SNR). This enables measurements to be made over longer propagation distances, thus overcoming the problem associated with low signal strength due to losses caused by absorption, reflection, refraction, and scattering of the ultrasound wave as it propagates through a medium.

Additionally, ultrasound transducers are generally very inefficient, and often need to be driven with high voltages to produce sufficient sound power. Comparing transmitted and received signals in this way significantly decreases the drive voltages carried on wires inside the catheters, effectively reducing both the electrical hazard to the patient, and the levels of potential electromagnetic interference. The output powers of small ultrasound transmitters are also limited by the need to avoid damage to neighbouring tissue.

Advantageously the predetermined waveform generated from each of said plurality of transducers are different with respect to each other, thereby facilitating contemporaneous detection of said signals.

The present invention allows for signals received contemporaneously from different transmitters to be separated and processed individually, provided the transmitted signals have known and distinguishable waveforms. For example, narrow band signals at different centre frequencies can be separated by bandpass filtering. This means that all the transmitting transducers could be activated contemporaneously, instead of sequentially, thus enabling all the times of flight measurements to be completed faster. This would have the ultimate effect of enabling the catheter location to be updated at a higher rate.

Advantageously, the data processor may operate to calculate a transfer function between the transmitted and received sound signals as a function of frequency. The transfer function depends on the characteristics of the media through which the sound travels, and in particular on the frequency dependent absorption coefficient. The transfer function measurements may be used to infer which sort of tissue the sound has travelled through and how much of each tissue type lies along its path. This information could then be used to make a more accurate estimate of the average speed of sound and hence the distance between the transmitting and receiving transducers. This leads to a better estimate of the catheter location inside the body.

According to an aspect of the present invention, there is provided a method of tracking a catheter head with reference to a part of the human or animal body, said method comprising the steps of disposing at least two of a plurality of spaced apart reference transducers at predetermined positions inside the human or animal body, inserting a catheter with at least one transducer disposed proximity the catheter head, inside said human or animal body, generating at least one signal from said plurality of reference transducers and or from said at least one transducer disposed on said catheter, detecting said at least one signal with said at least two reference transducers and or said at least one transducer disposed on said catheter, whereby the time of flight between said at least one transducer disposed on said catheter and said at least two of said plurality of spaced apart reference transducers at predetermined positions gives an indication of said location of said catheter with reference to said reference transducers, characterised by the steps of arranging for said at least one transmitted signal to have a predetermined waveform, and comparing said at least one transmitted signal generated by said at least one transmitter with said signal representative of said transmitted signal received by said at least one receiver, thereby improving an accuracy with which said time of flight of said signals is determined.

BRIEF DESCRIPTION OF THE DRAWING

While the principle advantages and features of the invention have been described above, a greater understanding and appreciation of the invention may be obtained by referring to the following drawings and detailed description of a preferred embodiment, presented by way of example only, in which.

DETAILED DESCRIPTION OF THE DRAWING

Figure 1:
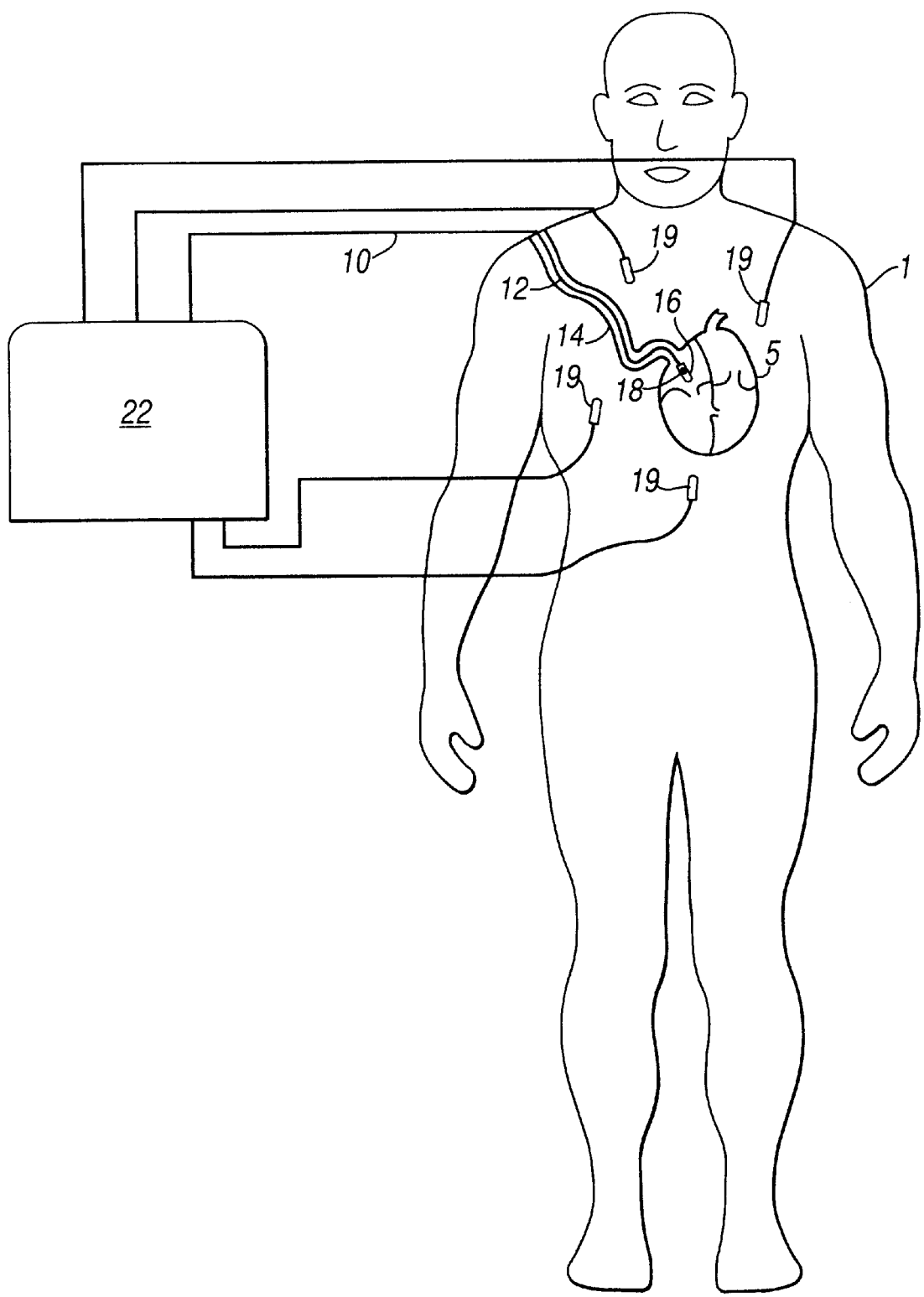
FIG. 1 is a schematic diagram of a catheter inserted in a human body.

FIG. 1 provides a schematic illustration of a catheter inserted into a human body 1, through an artery 14, and into a heart 5, which is one application for the catheter tracking system described by the present invention. In FIG. 1, a catheter 10 is shown to have generally a head 16, upon which is disposed a transducer 18. A plurality of reference transducers 19 are arranged around the heart 5 in a spaced apart relationship inside and/or outside the body 1. The catheter 10 is shown inserted into a human body 1, through an artery 14 and into a heart 5, for the purpose of performing some type of medical procedure, for example endocardiography.

Figure 2:
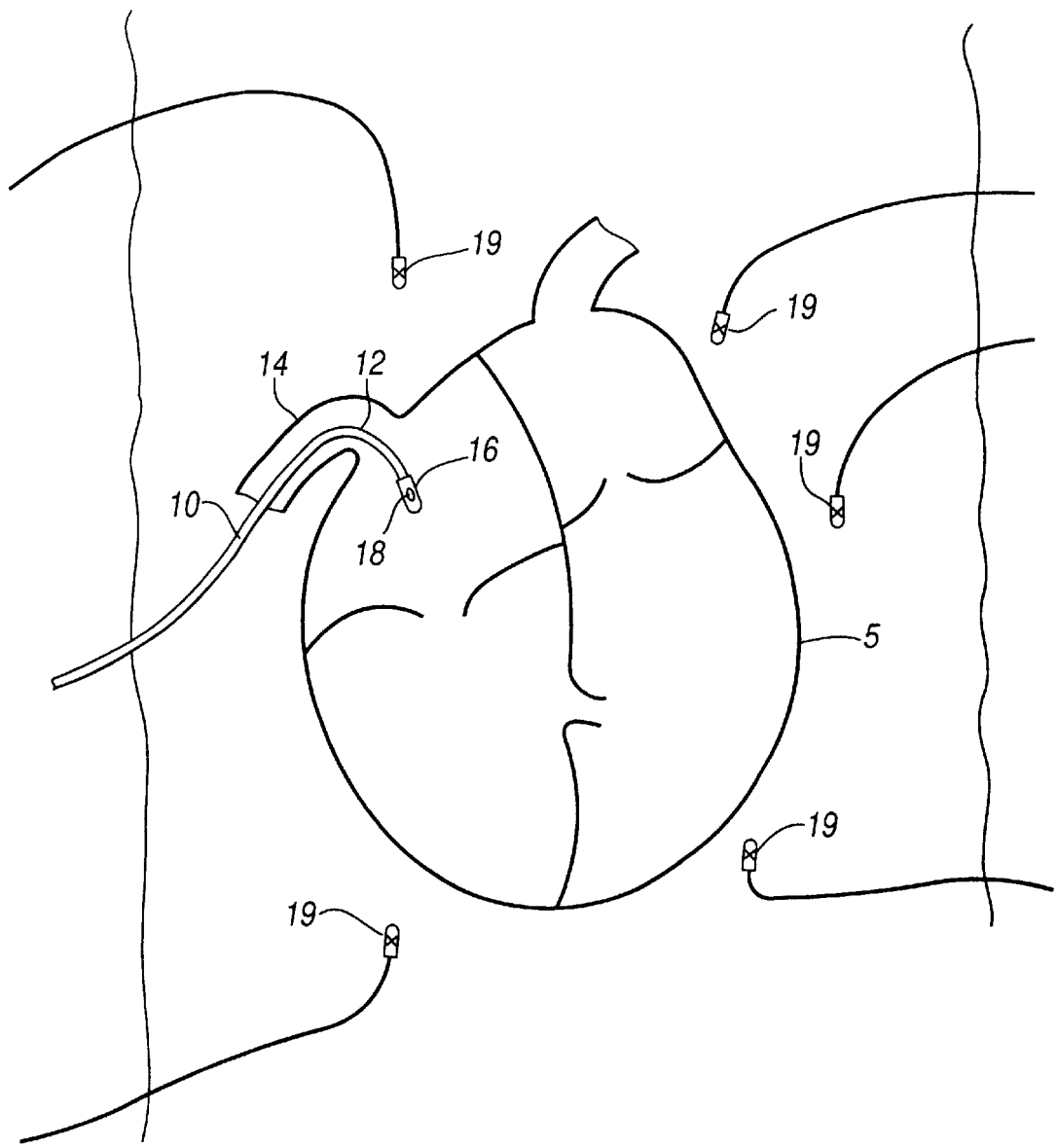
FIG. 2 shows a typical catheter inserted through an artery into a heart, with reference transducers located around the heart, and in particular one transducer located on the head of the catheter inserted into the heart.

FIG. 2 shows a close-up of the catheter shown in FIG. 1, where parts also appearing in FIG. 1 bear identical numerical designations. A catheter 10, is shown disposed within artery 14, and conveyed thereby into the heart 5. Located on the head of the catheter 16 is a transducer 18. Located around the heart 5 and in the proximity of the catheter 10, are a plurality of reference transducers 19.

Figure 3:
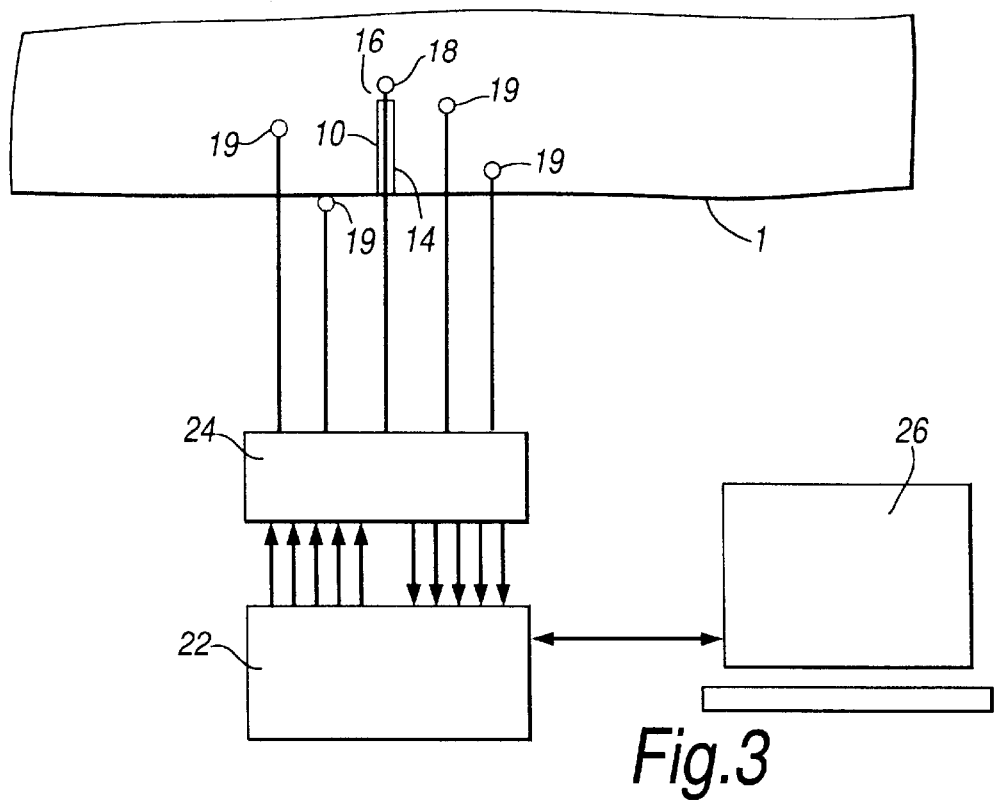
FIG. 3 shows a schematic diagram of the signal processing unit, in conjunction with several reference transducers located in and on the body as well as a catheter inserted in a part of a body with a single transducer located on the catheter head.

FIG. 3 shows essentially the same items as in FIG. 1 except in more detail, where parts also appearing in FIG. 1 bear identical numerical designations. A catheter 10 in inserted into a body 1 through an artery 14. A multi-channel transceiver 24 serves as an interface between a signal processing unit 22 and the plurality of transducers 18, 19 and operates to switch the transducers between a transmission mode, in which the transducers 18, 19 generate acoustic signals and a reception mode in which the transducers 18, 19 detect acoustic signals. Also attached to the signal processing unit 22 is a computer based user interface 26, which displays the catheter head's 16 position in the body 20, and other results calculated by a signal processor 22. The computer based user interface 26 accepts the user's commands to adjust various system parameters such as an interval between which acoustic signals are generated providing a corresponding update rate of a position of the catheter head.

Figure 4:
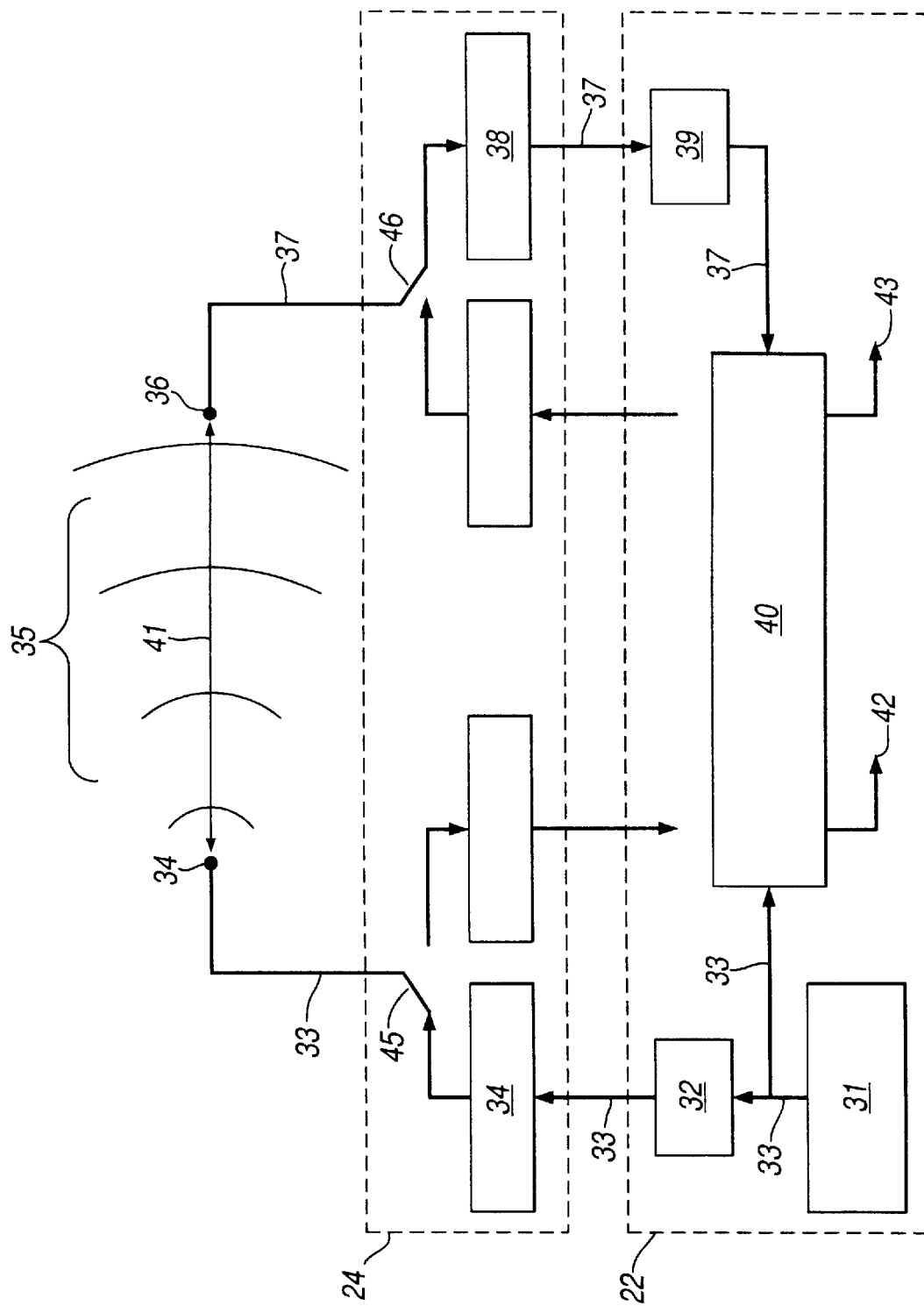
FIG. 4 shows a detailed drawing of the multi-channel transceiver and signal processing unit required for this catheter tracking system, and, FIG. 5 shows a typical scenario of distance measurements between four reference transducers and a single transducer located on the catheter head.

As depicted in FIG. 4, a signal processor 22 has a signal generator 31, which serves to generate signals with which the transducers are energised. The signal generator 31 is coupled to a multi-channel transceiver 24 via a digital-to-analogue converter (DAC) 32, which serves to generate an analogue signal representative of the digital signal provided by the signal generator 31. The generated signal 33 is transmitted to the multi-channel transceiver 24 where it is amplified by an amplification stage 34 and then passes a transmitting/receiving switch 45, which for this stage of the process is operating in transmission mode, before being sent to at least one of the plurality of transducers 34 (or as represented by 18 and 19 in FIGS. 1, 2 and 3), which are for this stage of the process operated in transmission mode. The transducer 34 operates to generate a sound wave 35, representative of the generated signal 33. At least one of the plurality of transducers 36 is then switched to receiving mode by the multi-channel transceiver 24 and the propagating sound wave 35 is received by said receiving transducer 36. A received signal 37, representative of the detected sound wave 35, is then returned to the multi-channel transceiver 24 where it passes another transmitting/receiving switch 46, this one operating in receiving mode. The received signal 37 is amplified by an amplification stage 38, and then converted back to digital format by an analogue-to-digital converter (ADC) 39 before being transmitted to the system identification processor 40. In addition, a portion of the original generated signal 33 is also sent to the system identification processor 40.

As will be appreciated by those skilled in the art, an alternative embodiment of the present invention might employ the use of analogue signals generated by a signal generator 31, and fed to transducers 18, 19. In this case the system identification processor 40 may convert these analogue signals to digital form.

Once a signal is propagated from one transducer 34 to another 36, the system identification processor 40 calculates the direct propagation time between these transducers from the digitised waveforms of the transmitted signal 33 and received signal 37. The straight line distance 41 between the transmitting transducer 34 and the receiving transducer 36, is then estimated by multiplying this time by an estimate of the average speed of sound over the propagation path. The straight line distance 41 is then sent as output data 42 from the system identification processor 40. If detailed knowledge is available of the anatomy between the transducers, the speed of sound estimates may be improved and/or a correction factor may be made for non straight line propagation. Should the generated signals be ultrasonic, such knowledge can be obtained via the system identification processor 40 owing to the frequency dependent ultrasonic absorption coefficient of tissue, thereby inferring the characteristics of said tissue in the propagation path.

Figure 5:
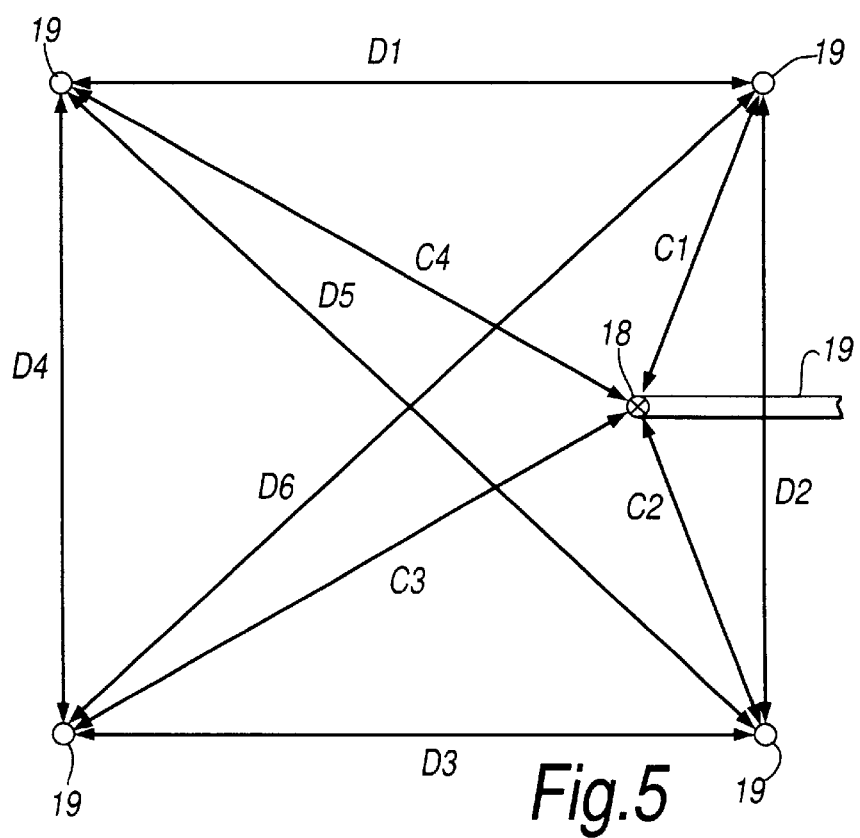

FIG. 5 shows an example of several straight line distance estimates D1, D2, D3, D4, D5, D6 between several pairs of reference transducers 19. Additionally, FIG. 5 shows several straight line distance measurements C1, C2, C3, C4 between the reference transducers 19 and a transducer located on the catheter head 18. By performing a triangulation calculation, which is well known within the art, an estimate is obtained of the relative location of all transducers involved in this set of measurements. If a minimum of four reference transducers 19 are used, a three dimensional reference frame can be defined relative to these reference transducers 19. The catheter mounted transducer 18 can then be located relative to this reference frame. Provided the reference transducers 19 are at known, fixed locations with respect to the anatomy of the body, the catheter may then be located relative to this anatomy.

The embodiment of the present invention provides significant advantages over known prior art systems. By arranging for the signal generated by the signal generator 31 to be fed to the system identification processor 40, a waveform shape of the sound wave generated by the transducer 34 is known apriori. As such, the system identification processor, is able to provide a substantial improvement in a time of flight measurement of the sound wave 35, between the transducer 34 and the transducer 36, by cross correlating the transmitted signal 33 with the received signal 37. By shifting the received signal in time, and determining a maximum peak of energy generated by a cross-correlator within the system identification processor 40, the time of flight is determined from a time shift corresponding to a temporal position associated with the maximum cross-correlation energy.

The generated signal 33, is selected so that an auto-correlation function of the signal produces a peak which can be easily detected in comparison with noise signals which will be generated by the transducer 36, and presented in the received signal 37. An example of signals producing appropriate auto-correlation functions is a 'chirp', in which the transmitted signal is shifted in frequency with respect to time in a predefined way. Cross-correlation with the received signal 37 will effectively de-chirp the transmitted signal, thereby providing a substantial improvement in an accuracy of the measurement of the time of flight of the signal. A further example of a waveform selected to provide an appropriate auto-correlation function is an M-sequence, which is a digital data sequence, which is selected and arranged to provide a significant peak in energy when cross correlated with a version of itself with zero temporal shift.

As will be appreciated, the position of the catheter head within the body should be updated to allow progress of the position of the catheter within the body to be monitored. Multiplexing is effected by transmitting different signals from multiple transducers simultaneously. These signals will then be received approximately simultaneously by one or more transducers, so that they overlap in the transducers' output signals. By appropriate processing of these output signals, the different transmitted signals may (effectively) be separated. Multiplexing of signals generated and detected by the transducers provides a means for substantially contemporaneous measurement of the times of flight of signals between respective transducers, thereby providing a substantial increase in a rate in which a position of the catheter head is updated. This will correspondingly allow movement of the catheter head to be tracked, more accurately.

As will appreciated by those skilled in the art, various other ways of multiplexing and de-multiplexing the signals can be used, such as code division multiplexing.

As will be appreciated by those skilled in the art, various modifications may be made to the embodiment hereinbefore described without departing from the scope of the present invention.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A catheter tracking system for locating and tracking a catheter head with reference to a part of the human or animal body, said catheter tracking system comprising:
    a plurality of spaced apart transducers, at least one of which is disposed on a catheter and at least two others of which are disposed at predetermined reference points; and
    a signal processing unit coupled to the plurality of spaced apart transducers and arranged to selectively enable individual ones of said plurality of spaced apart transducers to operate as either a transmitter or a receiver, and to energize at least one of the transmitters to generate at least one transmitted signal which is detected by at least one of said receivers, a time of flight of the at least one transmitted signal generated by the at least one transmitter and received by the at least one receiver being indicative of a distance between said at least one transmitter and said at least one receiver, and times of flight between the at least one transducer disposed on the catheter and the at least two other transducers disposed at said predetermined reference points providing an indication of the location of the catheter with reference to said reference transducers; wherein, the at least one transmitted signal has a predetermined waveform;

the signal processing unit compares the at least one transmitted signal generated by said at least one transmitter with a signal representative of the transmitted signal received by the at least one receiver, and determines the time of flight of the at least one transmitted signal based on a result of said comparison; and said comparison is performed using cross-correlation of pairs of transmitted and received signals, with the received signal being shifted in time, a maximum peak of energy resulting from the cross-correlation being detected, and the time of flight being determined from a time shift corresponding to a temporal position of maximum cross-correlation energy.

2. A catheter tracking system as claimed in claim 1, wherein said at least one signal generated is acoustic.

3. A catheter tracking system as claimed in claim 1, wherein said acoustic signal is ultrasonic.

4. A catheter tracking system as claimed in claim 1, wherein said predetermined waveforms generated from each of said plurality of transducers are different with respect to each other, said difference facilitating contemporaneous detection of said signals, thereby facilitating determination of said catheter head location at a faster rate.

5. A catheter tracking system as claimed in claim 4, wherein each of said predetermined waveforms generated from each of said plurality of transducers is different with respect to a change in frequency with respect to time.

6. The catheter tracking system as claimed in claim 1, wherein said transmitted signal comprises one of:

a signal which is shifted in frequency with respect to time in a predetermined manner; and digital data in the form of an M-sequence.

7. A catheter tracking system for locating and tracking a catheter head with reference to a part of the human or animal body, said catheter tracking system comprising:

a plurality of spaced apart transducers, at least one of which is disposed on a catheter and at least two others of which are disposed at predetermined reference points; and a signal processing unit coupled to the plurality of spaced apart transducers and arranged to selectively enable individual ones of said plurality of spaced apart transducers to operate as either a transmitter or a receiver, and to energize at least one of the transmitters to generate at least one transmitted signal which is detected by at least one of said receivers, a time of flight of the at least one transmitted signal generated by the at least one transmitter and received by the at least one receiver being indicative of a distance between said at least one transmitter and said at least one receiver, and times of flight between the at least one transducer disposed on the catheter and the at least two other transducers disposed at said predetermined reference points providing an indication of the location of the catheter with reference to said reference transducers; wherein, the at least one transmitted signal has a predetermined waveform;

the signal processing unit compares the at least one transmitted signal generated by said at least one transmitter with a signal representative of the transmitted signal received by the at least one receiver, and determines the time of flight of the at least one transmitted signal based on a result of said comparison;

predetermined waveforms generated from each of said plurality of transducers are different with respect to each other, said difference facilitating contemporaneous detection of said signals, thereby facilitating determination of said catheter head location at a faster rate; and each of said predetermined waveforms generated from each of said plurality of transducers comprises a different one of a set of substantially orthogonal digital sequences.

8. The catheter tracking system as claimed in claim 7, wherein said comparison is performed using cross-correlation of pairs of transmitted and received signals, with the received signal being shifted in time, a maximum peak of energy resulting from the cross correlation being detected and the time of flight being determined from a time shift corresponding to a temporal position of maximum cross-correlation energy.

9. A catheter tracking system for locating and tracking a catheter head with reference to a part of the human or animal body, said catheter tracking system comprising:

a plurality of spaced apart transducers, at least one of which is disposed on a catheter and at least two others of which are disposed at predetermined reference points; and a signal processing unit coupled to the plurality of spaced apart transducers and arranged to selectively enable individual ones of said plurality of spaced apart transducers to operate as either a transmitter or a receiver, and to energize at least one of the transmitters to generate at least one transmitted signal which is detected by at least one of said receivers, a time of flight of the at least one transmitted signal generated by the at least one transmitter and received by the at least one receiver being indicative of a distance between said at least one transmitter and said at least one receiver, and times of flight between the at least one transducer disposed on the catheter and the at least two other transducers disposed at said predetermined reference points providing an indication of the location of the catheter with reference to said reference transducers; wherein, the at least one transmitted signal has a predetermined waveform;

the signal processing unit compares the at least one transmitted signal generated by said at least one transmitter with a signal representative of the transmitted signal received by the at least one receiver, and determines the time of flight of the at least one transmitted signal based on a result of said comparison; and said signal processing unit operates to determine a frequency dependent transfer function between transmitting and receiving transducers, providing information about the media through which said signal has propagated.

10. A catheter tracking system as claimed in claim 9, wherein said signal processing unit further operates to determine absorption coefficient data representative of said media through which said signal has propagated, and advantageously adjusts said distance measurements consequent upon said time of flight of said signal in combustion with said absorption coefficient data.

11. A method of tracking a catheter head with reference to a part of the human or animal body, said method comprising:

disposing at least two of a plurality of spaced apart reference transducers at predetermined positions with a reference to the human or animal body;

inserting a catheter with at least one transducer disposed proximate the catheter head, inside the human or animal body;

generating and transmitting at least one signal from the plurality of reference transducers or from the at least one transducer disposed on said catheter, said transmitted signal including a predetermined waveform;

detecting the at least one signal, including the predetermined waveform, with the at least two reference transducers or the at least one transducer disposed on said catheter, whereby a time of flight between the at least one transducer disposed on the catheter and the at least two of the plurality of spaced apart reference transducers at predetermined positions gives an indication of the location of said catheter with reference to the reference transducers;

comparing the at least one transmitted signal generated by the at least one transmitter with a signal representative of the transmitted signal received by the at least one receiver; and determining the time of flight of the at least one transmitted signal based on a result of said comparison;

wherein said comparison is performed using cross-correlation of pairs of transmitted and received signals, with the received signals being shifted in time, a maximum peak of energy resulting from the cross-correlation being detected, and the time of flight being determined from a time shift corresponding to a temporal position of maximum cross-correlation energy.

12. A method of tracking a catheter head as claimed in claim 10, wherein the steps of comparing said generated and said received signals is done by cross-correlation of pairs of transmitted and received signals.

13. A method of tracking a catheter head as claimed in claim 12, further comprising generating said predetermined waveforms which differ from each other, said difference facilitating contemporaneous detection of said signals, thereby facilitating the determine of said catheter head location at a faster rate.

14. The method as claimed in claim 11, wherein said transmitted signal comprises one of:

a signal which is shifted in frequency with repect to time in a predetermined manner; and digital data in the form of an M-sequence.

* * * * *